United States Patent [19]

Kleiman

[11] 4,044,113

[45] Aug. 23, 1977

[54] PREPARATION OF BROMINE

[75] Inventor: Joseph P. Kleiman, Birmingham, Mich.

[73] Assignee: Ethyl Corporation, Richmond, Va.

[21] Appl. No.: 658,839

[22] Filed: Feb. 17, 1976

[51] Int. Cl.$^2$ .................. C01B 7/10; C07C 17/20
[52] U.S. Cl. .................. 423/500; 423/502; 260/658 R
[58] Field of Search .................. 260/658 R; 423/502

[56] References Cited

U.S. PATENT DOCUMENTS

| 3,000,980 | 9/1961 | Asadorian et al. | 260/658 R |
|---|---|---|---|
| 3,370,096 | 2/1968 | Donaldson et al. | 260/658 R |
| 3,607,958 | 9/1971 | Forman et al. | 260/658 R |
| 3,641,172 | 2/1972 | Johnson et al. | 260/658 R |
| 3,961,033 | 6/1976 | Kleiman et al. | 260/658 R |

Primary Examiner—Edward Stern
Attorney, Agent, or Firm—Donald L. Johnson; John F. Sieberth; Robert A. Linn

[57] ABSTRACT

Bromine is produced by reacting chlorine and ethylene dibromide in the presence of an iron halide catalyst, e.g. ferric chloride.

9 Claims, No Drawings

PREPARATION OF BROMINE

BACKGROUND OF THE INVENTION

Because bromine is corrosive, its storage and shipment requires special vessels and precautions. This invention pertains to means for recovering bromine from ethylene dibromide, a compound that is readily stored and shipped. The reaction employed to recover bromine is simple to carry out and requires common reactants. 1-Bromo-2-chloroethane is a byproduct.

Israeli Pat. No. 17898 is directed to bromine recovery. It markedly differs from the present process in (1) specifying a bromoalkane having either two bromines linked to the same carbon or three bromine atoms in the molecule, and (2) using antimony pentachloride as a chlorine source. In U.S. Pat. No. 3,961,033, issued June 1, 1976, applicant and Kestutis A. Keblys disclose bromine is produced by reacting chlorine and ethylene dibromide in the presence of an aluminum halide catalyst, e.g. aluminum chloride. A small amount of bromine present prior to chlorine addition shortens the induction period. Some decomposition of the organic product occurs if it is distilled in the presence of aluminumcontaining residues. These residues can be removed by water wash which can be followed by drying with $H_2SO_4$. After such treatment, ethylene dichloride can be recovered by distillation without substantial decomposition.

SUMMARY OF THE INVENTION

This invention pertains to a process for preparing bromine comprising reacting chlorine with ethylene dibromide in the presence of a catalytic quantity of iron halide. The catalyst is selected from ferric chloride, ferric bromide, and ferric chlorobromides. The process is conducted under substantially anhydrous conditions.

Thus, this invention provides means for bromine generation from ethylene dibromide by a halogen exchange reaction with chlorine. Ferric chloride is a preferred catalyst. Without being bound by any theory, the reaction is depicted as follows:

DESCRIPTION OF PREFERRED EMBODIMENTS

Because of the greater convenience and better reaction control, chlorine is preferably added to a mixture of iron halide and $BrCH_2CH_2Br$. However, other addition modes can be used. Thus, if desired, ethylene dibromide can be pressure injected into a vessel that contains chlorine under pressure and iron halide.

In the preferred addition mode, chlorine is added under the liquid surface at a rate such that the added chlorine does not bubble out of the resultant mixture throughout the reaction period. In other words, the rate of addition is lower than that which causes constant "breakthrough". Stated another way, the preferred mode of chlorine addition is at a rate at which substantially all the chlorine is utilized upon contact by the reaction liquid.

Although avoidance of breakthrough, especially at beginning reaction stages, is preferred, it is not critical. Thus, breakthrough can be allowed to occur, especially in situations when advantageous to do so and where there are no untoward complications from the excess chlorine admitted. Thus, when using a series of reaction vessels, chlorine breakthrough can be used in some (or all) the vessels to achieve chlorine passage throughout the vessel series. Furthermore, as explained below, molar excesses of chlorine can be used. When this expedient is employed, breakthrough will occur, especially toward the end of the reaction period.

Summarizing, the rate of chlorine addition is not critical. However, for economical reasons, it is desirable to avoid chlorine wastage or unnecessary chlorine recovery and this can be accomplished by minimizing breakthrough. Furthermore, by controlling the rate of chlorine addition, the reaction rate is controllable; therefore, one can use the chlorine addition rate to minimize complications from too fast a reaction rate. Therefore, it is desirable to add chlorine at a rate at which all or substantially all the chlorine is utilized upon contact by the reaction liquid. To save time, one can add the chlorine at the maximum rate at which complete or substantially complete absorption takes place. When an excess of chlorine is used, breakthrough can occur, especially at later reaction stages, and such breakthrough is expected. Likewise, some breakthrough may occur during any induction period.

To determine whether chlorine addition is proceeding at a desirable rate, the addition can be visually followed by observing through a transparent portion of the reaction vessel wall or by inspection of a bubbling or similar device which indicates flow from the reaction vessel.

In general, it is desirable to use at least one mole portion of chlorine per each two mole portion of $BrCH_2CH_2Br$. Using substantially less chlorine results in recovery of substantially less bromine, and when bromine recovery is the prime object, this may be economically unattractive.

To obtain the maximum amount of bromine from ethylene dibromide, an excess of chlorine can be used. There is no real upper limit on the excess amount of chlorine and this is governed by such secondary considerations as economics. Generally, there is no real advantage to using a great excess of chlorine per mole of ethylene dibromide and in most intances, the reaction proceeds well when less excess chlorine is employed. Thus, preferably from 0.5 to 0.8 moles of chlorine are used per mole of ethylene dibromide, more preferably from 0.5 to 0.6 moles.

For the process to proceed at a suitable rate, a catalyst is used. Efficacious catalysts are iron halides. Of these, iron chloride, iron bromide, and iron chlorobromides are preferred, especially the ferric compounds. Of the three halogens per molecule in the ferric chlorobromides, one or two are chlorine and the remainder are bromine. Of the halides mentioned, $FeCl_3$ and $FeBr_3$ are preferred with $FeCl_3$ being most preferred.

A catalytic amount of catalyst is employed. By catalytic amount is meant a quantity which gives a suitable reaction rate. The exact amount of catalyst is not critical. For example, there is no real upper limit on the amount of iron halide employed; this being governed by such secondary considerations as economics and reaction vessel size. Generally, it is preferable to employ the least amount of catalyst which allows the reaction to proceed at a utilizable rate. Thus, for example, iron chloride concentrations of about 0.5–2.0 weight per cent, preferably about 0.6 to 2.0 weight per cent based on the weight of the ethylene dibromide charged, are employed. Greater or lesser concentrations can be employed if desired.

When using another of the catalysts mentioned above, the concentration employed is about the same, taking into consideration differences in molecular weight and activity between the catalysts.

The process proceeds well at atmospheric pressure; however, greater or lesser pressures can be used if desired. In general, there is no real advantage to conducting the process under vacuum. As already referred to, the process can be conducted at superatmospheric pressure, say, up to 100 psi or higher, but utilizing a suitable reaction vessel pressurized with chlorine. Thus, one can initially add iron halide catalyst and chlorine to a pressure vessel and add ethylene dibromide reactant at a desired rate, using means which allow addition to take place against the pressure in the vessel. However, for this expedient, the equipment cost is greater. Summarizing, the reaction pressure is not critical and the process proceeds well under ambient or substantially ambient pressures.

Reaction temperature is not critical. A suitable temperature affords a reasonable reaction rate and does not cause an undesirable amount of product or reactant decomposition. The process proceeds at ambient temperatures, and slightly lower and slightly elevated temperatures can be used. Normally, slightly elevated temperatures are used to obtain a faster reaction rate. Thus, in general, a suitable temperature is between 30° and 100° C.; more preferably between about 35° and about 60° C., most preferably 35°-50° C.

After initiation, the reaction is exothermic, and cooling means can be employed to keep the reaction within the desirable temperature range. Furthermore, the temperature can be regulated to an appreciable extent by the chlorine addition rate. In general, chlorine is added over a period of from about 15 minutes to 5 hours; from one-half to three hours normally suffices.

To facilitate reaction, the reactants are efficiently contacted. In some instances, the amount of reaction mixture obtained by chlorine addition is insufficient. In such instances, ancillary agitation means, such as stirring or rocking, can be utilized.

The reaction proceeds best in the absence of a substantial amount of water. In other words, better results are achieved under substantially anhydrous conditions. It is unnecessary to rigorously exclude water. Thus, chlorine and ethylene dibromide of normally available commercial grades can be employed. Furthermore, commercially available grades of anhydrous aluminum halides can be used. In general, the amount of water should not exceed 0.1 weight per cent, based on the weight of reactants and catalyst charged. However, it is to be understood that the reaction will tolerate a minor amount of water as indicated above.

There are two main products of the process, viz, bromine and an organic fraction, which is largely ethylene chlorobromide. Bromine and ethylene chlorobromide can be recovered from the reaction zone by well known techniques, such as distillation.

The following example serves to illustrate the invention and not limit it.

EXAMPLE

To a mixture of 351.3 g of ethylene dibromide and 5.0 g of anhydrous ferric chloride was added 130 g of chlorine. The addition took two hours and the maximum temperature was 39°. Chlorine breakthrough was noted for most of this period. More chlorine was lost due to a plug in the system. The mixture at the end of reaction weighed 454.7 g (theory 486.3 g). Analysis indicated that the final mixture contained about 163 g or bromine and 38.5 g of chlorine. VPC analysis of the organics gave a trace of ethylene dichloride, 98.1 per cent 1-bromo-2-chloroethane, 1.5 per cent ethylene dibromide and traces of unknowns.

Similar results are obtained when the amount of chloride used per mole of ethylene dibromide is from about 0.5 to about 0.6 moles.

Similar results are obtained when the process of the above example is repeated except that the catalyst used is iron (III) bromide or an iron (III) chlorobromide, the amount of catalyst being from about 0.5–2.0 weight per cent based on the weight of ethylene dibromide charged.

Similar results are obtained when the above process is repeated using a reaction temperature between about 35° and about 60° C. and the reaction time is from one-half to three hours.

The process of the above example proceeds efficaciously if the amount of water does not exceed 0.1 weight per cent.

As appreciated by a skilled practitioner, elemental bromine and chlorine can react in equimolar quantities to form bromine chloride. Hence, when bromine and chlorine are both present, say, at the end of a process conducted in accordance with this invention, bromine chloride can be formed. However, bromine chloride can be transformed into the elemental halogens by distillation.

I claim:

1. Process for preparing bromine comprising reacting chlorine with ethylene dibromide in the presence of a catalytic quantity of iron halide selected from ferric chloride, ferric bromide and ferric chlorobromides.

2. Process of claim 1 wherein the iron halide is ferric chloride.

3. Process of claim 2 wherein the amount of ferric chloride is about 0.5–2.0 weight per cent.

4. Process of claim 2 wherein the amount of ferric chloride is about 0.6 to about 2.0 weight per cent.

5. Process of claim 1 being conducted at from about 35° to about 60° C.

6. A process for preparing bromine in substantial accordance with the equation

said process being conducted by introducing a gas consisting substantially of chlorine into a reaction zone initially substantially consisting of ferric chloride and liquid ethylene dibromide such that said gas is introduced under the surface of liquid in said zone at a rate at which substantially complete utilization of said gas in said liquid takes place, said process being conducted at a temperature between about 35° and about 60° C., the amount of $FeCl_3$ being from about 0.6 to 2.0 weight per cent based on the weight of ethylene dibromide.

7. Process for preparing bromine and 1-bromo-2-chloroethone, said process comprising reacting chlorine with ethylene dibromide in the presence of a catalytic quantity of ferric chloride.

8. A process of claim 7 being conducted at from about 35° to about 60° C.

9. A process of claim 8 being further characterized by use of from about 0.6 to about 2.0 weight per cent ferric chloride.